US012789015B2

(12) United States Patent
Zhang et al.

(10) Patent No.: US 12,789,015 B2
(45) Date of Patent: Nov. 10, 2026

(54) SMALL ANIMAL FLASH RADIOTHERAPY IRRADIATOR AND INVERSE GEOMETRY MICRO-CT

(71) Applicant: Washington University, St. Louis, MO (US)

(72) Inventors: Tiezhi Zhang, St. Louis, MO (US); Yuewen Tan, St. Louis, MO (US); Shuang Zhou, St. Louis, MO (US); Qinghao Chen, St. Louis, MO (US); Jonathan Haefner, St. Louis, MO (US)

(73) Assignee: Washington University, St. Louis, MO (US)

( * ) Notice: Subject to any disclaimer, the term of this patent is extended or adjusted under 35 U.S.C. 154(b) by 129 days.

(21) Appl. No.: 18/843,600

(22) PCT Filed: Apr. 21, 2023

(86) PCT No.: PCT/US2023/019367

§ 371 (c)(1),
(2) Date: Sep. 3, 2024

(87) PCT Pub. No.: WO2023/205395

PCT Pub. Date: Oct. 26, 2023

(65) Prior Publication Data

US 2025/0170426 A1 May 29, 2025

Related U.S. Application Data

(60) Provisional application No. 63/333,776, filed on Apr. 22, 2022.

(51) Int. Cl.

*A61N 5/10* (2006.01)
*A61B 6/03* (2006.01)
*A61B 6/50* (2024.01)

(52) U.S. Cl.

CPC ............ *A61N 5/1084* (2013.01); *A61B 6/032* (2013.01); *A61B 6/508* (2013.01); *A61N 5/1049* (2013.01); *A61N 2005/1054* (2013.01)

(58) Field of Classification Search

CPC ........ A61N 5/1084; A61B 6/032; A61B 6/508
See application file for complete search history.

(56) References Cited

U.S. PATENT DOCUMENTS 8,173,983 B1 5/2012 Sahadevan
9,636,525 B1 5/2017 Sahadevan et al.
(Continued)

FOREIGN PATENT DOCUMENTS

CN 107626048 A 1/2018
CN 110732094 A 1/2020
(Continued)

OTHER PUBLICATIONS

International Search Report and Written Opinion issued for Serial No. PCT/US2023/019367, dated Aug. 7, 2023 (14 pages).

*Primary Examiner* — Hugh Maupin
(74) *Attorney, Agent, or Firm* — Armstrong Teasdale LLP

(57) ABSTRACT

A small animal imaging and radiotherapy (RT) irradiator device uses a circular array x-ray source to scan an anatomy of an animal, delivers conventional and ultra-high dose rate of radiation to the treatment target. The multipixel x-ray source includes a ring of focal spots capable of irradiating x-ray beams from around fifty beam angles. The x-ray beams are collimated with a collimator designed in treatment planning.

19 Claims, 9 Drawing Sheets

(56) References Cited

U.S. PATENT DOCUMENTS

| | | | | |
|---|---|---|---|---|
| 11,554,271 | B2 * | 1/2023 | Smith | A61N 5/1045 |
| 11,766,574 | B2 * | 9/2023 | Vanderstraten | A61N 5/103<br>600/1 |
| RE50,811 | E * | 3/2026 | Fahrig | A61N 5/1084 |
| 2009/0196393 | A1 * | 8/2009 | Wang | G06T 12/20<br>378/4 |
| 2010/0260317 | A1 | 10/2010 | Chang et al. | |
| 2020/0353288 | A1 | 11/2020 | Shaw et al. | |
| 2022/0323793 | A1 * | 10/2022 | Brooks | A23B 4/015 |
| 2023/0201630 | A1 * | 6/2023 | Spiessens | A61N 5/1039<br>600/1 |
| 2023/0390587 | A1 * | 12/2023 | Wong | A61N 5/1077 |
| 2024/0090112 | A1 * | 3/2024 | Agustsson | G21K 5/10 |

FOREIGN PATENT DOCUMENTS

| | | | |
|---|---|---|---|
| CN | 212214394 | U | 12/2020 |
| JP | 2007530077 | A | 11/2007 |
| JP | 2009538204 | A | 11/2009 |
| KR | 10-2021-0041587 | A | 4/2021 |
| WO | 2021061666 | A1 | 4/2021 |

* cited by examiner

SMALL ANIMAL FLASH RADIOTHERAPY IRRADIATOR AND INVERSE GEOMETRY MICRO-CT

CROSS-REFERENCE TO RELATED APPLICATIONS

This application is a U.S. National Stage Entry of International Patent Application No. PCT/US2023/019367, filed Apr. 21, 2023, which claims priority to U.S. Provisional Patent Application Ser. No. 63/333,776, filed Apr. 22, 2022, the entire disclosures of which are hereby incorporated by reference in their entirety.

FIELD OF THE DISCLOSURE

The field of the disclosure relates generally to radiation therapy and, more specifically, a flash radiotherapy (FLASH-RT) system for preclinical research based on a multipixel x-ray source. The field of disclosure also relates generally to a micro-CT imaging device for preclinical research based on multipixel x-ray source.

BACKGROUND

Radiation therapy (RT), or radiotherapy, is one of the most widely-used and successful cancer treatment modalities, with 52% of cancer patients receiving at least one course of RT. However, there are also many scenarios in which durable local-regional control is compromised by normal tissue complications, e.g., locally-advanced tumors of the head and neck, lung, cervix, brain, and prostate. The need for improved therapeutic ratio in RT has driven important advances in ultra-high dose rate RT or Flash-RT technology that has been proven the advantage of improved therapeutic ratio. A small animal FLASH-RT system is needed for preclinical of FLASH-RT.

Conventional small animal irradiator systems have provided an ultra-high dose rate using a commercially available imaging x-ray tube. This type of single source x-ray tube is barely useful in real biological study since its fast dose falloff and thus a very small volume of FLASH radiation. It will be hard for many comparative studies which require much larger and deeper FLASH irradiation volume and for the commercial x-ray tubes.

In another design, combining two commercially available and rotatable x-ray tubes with rotating anode facing each other was provided. It required the phantom being very close to the sources. The FLASH dose region had a more uniform dose rate distribution compared with the above-mentioned system.

One example of a commercial system is the Small Animal Radiation Research Platform (Xstrahl Inc., Suwanee, GA) that can produce ~0.05 Gy/s dose rate at the isocenter located at 35 cm nominal source-to-surface distance (SSD). Bazalova-Carter and Esplen studied feasibility of achieving UHDR in a commercially available x-ray tube with a fixed anode. In a later development of a kV FLASH tube for in vitro irradiations, x-ray beams were controlled by a shutter to deliver FLASH irradiations in pulses. This design is not practical for in vivo studies as UHDR is only achieved within a few mm of the surface due to the small SSD that results in fast dose falloff due to beam divergence. Rezaee et al. proposed a kV FLASH design consisting of two commercial diagnostic x-ray tubes with rotating anodes facing each other. This design requires the phantom to be attached to the surfaces of both tubes. Pulsed photon FLASH beam could be delivered uniformly in a water phantom in 20 mm spacing between two tube surfaces. However, the conformity of the dose to the target is subpar due to limited beam angles. Also, none of the mentioned methods can deliver x-ray beams in either well-defined macro-pulses or continuous current (DC) mode of operation. The lack of small animal FLASH irradiator that can mimic clinical FLASH-RT greatly hinders the biological study of FLASH-RT and clinical translations. What is needed is a system to reach a FLASH dose rate that is also flexible to control an inversely optimized dose distribution.

BRIEF SUMMARY

The present embodiments may relate to, inter alia, systems and methods for a flash radiotherapy (FLASH-RT) device to provide treatment. The present embodiments provide treatment by a FLASH-RT device that spares normal tissue when killing cancer cells. This may be performed by using the FLASH-RT device to deliver radiation at an ultra-high dose rate by irradiating the target simultaneously by all sources. Additionally, or alternatively, the FLASH-RT device may deliver radiation at a conventional dose rate. For example, the FLASH-RT device may provide a conventional dose rate by sequentially scanning the sources or adjusting the beam current.

In one embodiment, a flash radiotherapy (RT) irradiator system is described. The flash RT irradiator system including a multipixel x-ray source, a flash RT device connected to the multipixel x-ray source. The flash RT device is configured to scan an anatomy of an animal, and deliver, using the multipixel x-ray source, radiation at an ultra-high dose rate to a treatment location of the scanned anatomy.

In another embodiment, a method is described for delivering radiation to an animal. The method includes scanning, using a flash RT device, an anatomy of an animal and delivering, using a multipixel x-ray source, radiation at an ultra-high dose rate to a treatment location of the scanned anatomy.

In another embodiment, an inverse-geometry micro-CT system is described including a multipixel circular x-ray source array, a rotatable detector array, and a rotatable multi-aperture collimator configured to direct x-ray beams from the multipixel x-ray source to the rotatable detector array, wherein the multi-aperture collimator is an arc shaped collimator including a plurality of slot openings configured to rotate to scan an animal.

In yet another embodiment, a method of scanning small animal is described. The method includes scanning a plurality of partial focal spots of a circular x-ray source array, collimating, with a rotatable multi-aperture collimator, the x-ray source array to a detector, rotating the collimator and detector to another angle, repeating scanning the plurality of partial focal spots at the other angle, and reconstructing a plurality of 3D C T images using data measured by the detector.

Advantages will become more apparent to those skilled in the art from the following description of the preferred embodiments which have been shown and described by way of illustration. As will be realized, the present embodiments may be capable of other and different embodiments, and their details are capable of modification in various respects. Accordingly, the drawings and description are to be regarded as illustrative in nature and not as restrictive.

BRIEF DESCRIPTION OF THE DRAWINGS

The FIGURES described below depict various aspects of the systems and methods disclosed therein. Each figure depicts an embodiment of a particular aspect of the disclosed systems and methods, and that each of the FIGURES is intended to accord with a possible embodiment thereof. Further, wherever possible, the following description refers to the reference numerals included in the following FIGURES, in which features depicted in multiple FIGURES are designated with consistent reference numerals.

There are shown in the drawings arrangements which are presently discussed, it being understood, however, that the present embodiments are not limited to the precise arrangements and are instrumentalities shown.

Figure 1:
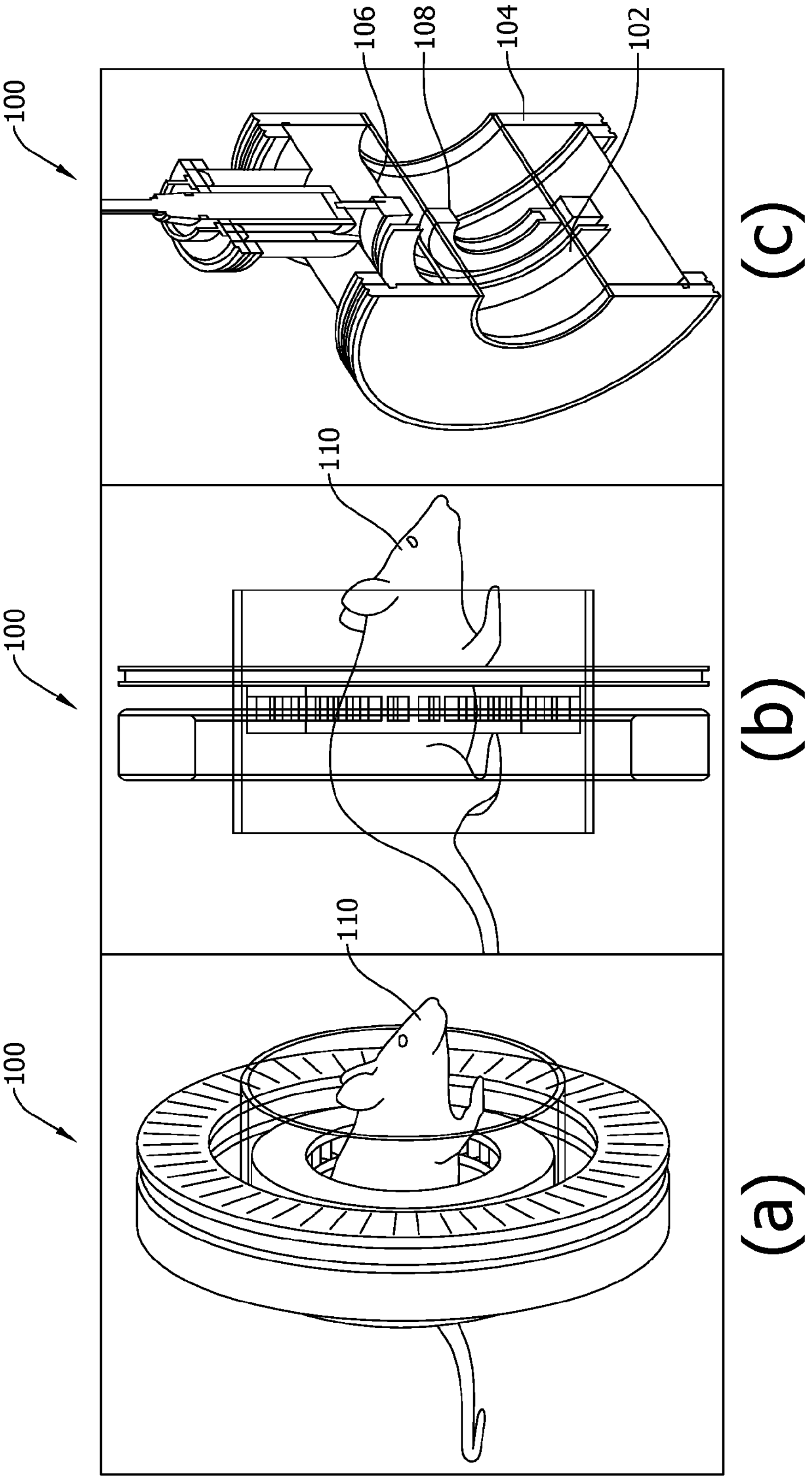
FIG. 1 illustrates an exemplary flash small animal irradiator based on a multipixel x-ray source.

The FIGURES depict preferred embodiments for purposes of illustration only. One skilled in the art will readily recognize from the following discussion that alternative embodiments of the systems and methods illustrated herein may be employed without departing from the principles described herein.

DETAILED DESCRIPTION

The present embodiments are related to, inter alia, systems and methods for providing a flash radiotherapy (RT) irradiator device using a multipixel x-ray source. In one exemplary embodiment, a method may be provided that uses a flash radiotherapy (RT) irradiator device that may use a multipixel x-ray source to scan an anatomy of an animal, determine a treatment location of the animal, and deliver an ultra-high dose of radiation to the animal's treatment location. The multipixel x-ray source may include a ring of focal spots capable of irradiating x-ray beams from around fifty beam angles. The x-ray beams may be collimated with a 3D printed collimator of the animal's anatomy.

One discovery in radiation oncology is the normal tissue complication-probability (NTCP) reduction effect of FLASH-RT. Comparing with conventional dose rate (CDR), ultra-high dose rates (UHDR) correspond to dose rates greater than 40 Gy/s and substantially improve normal tissue sparing while maintaining high tumor control probability (TCP). In some embodiments, FLASH-RT has the potential to significantly widen the TCP-NTCP therapeutic window, allowing dose intensification via hypofractionation. Proton is an example FLASH-RT modality, especially for small targets.

In at least one embodiment, a small animal irradiation platform is provided to deliver the same conformal dose distribution with different temporal structures including pulsed and continuous in CDR and UHDR modes. In some embodiments, platforms for preclinical FLASH investigations include but are not limited to (a) UHDR 8-15 MeV electron beams from clinical linear accelerators (linacs) (x-ray beam currents with target and flattening filter removed) and (b) clinical proton beam platforms (with enhanced beam currents and stationary beam modulators) able to produce UHDR spread-out Bragg peaks (SOBP) for both passively scattered and pencil-beam scanning (PBS) proton fields.

In some embodiments, a small animal FLASH irradiator based on distributed x-ray source technology is provided. In this exemplary embodiment, a multi-pixel thermionic emission x-ray (MPTEX) source is provided. An MPTEX source is based on thermionic cathodes. Even with as many as 50 cathodes, the power consumed by thermionic cathodes is only a fraction of the power produced by focal spots. An example application of an MPTEX source is a Tetrahedron Beam CT (TBCT), an imaging technique that can produce superior image quality in a similar footprint to Cone Beam CT (CBCT) imaging.

In another example, small animal FLASH irradiator (SAFI) is based on an MPTEX source. Based on a linear MPTEX source for TBCT imaging, a SAFI system comprises a circular array of x-ray sources. By orienting all sources toward the center of the focal spot circle, conformal UHDR treatments can be realized in application to mouse RT. The same circular source array can also be used for inverse-geometry micro-CT (IGMCT) onboard imaging. As many as 51 x-ray sources can be generated on a circle of 10 cm radius. The FLASH-RT treatment plan can be optimized analogously to clinical Intensity Modulated RT (IMRT) treatment plans.

The SAFI system, in some embodiments, is integrated with an IGMCT. Besides used for treatment planning simulation and setup for small animal irradiation, micro-CT may also be used as an in vivo imaging tool for biomedical research in general. X-ray exposure is a major concern for diagnostic CT. According to Rose's model, the radiation exposure increases cubically with the image resolution. The radiation dose by a micro-CT scan with resolution better than 100 micron is often too high for live animals. In one example, the annular-array x-ray source of the SAFI system is an in-plane fluence modulation supported by IGMCT. In this example, the system only needs to image a small region-of-interest (ROI) in the animal body. Conventional CT and micro-CT have to deliver an almost uniform dose to the whole body in order to avoid data truncation problem. The disclosed IGMCT can modulate in-plane x-ray intensity so that only the beams passing through the ROI have higher flux. IGMCT with x-ray fluence modulation will minimize radiation exposure to peripheral organs and tissues and achieve low-dose micro-CT imaging. Further, the example IGMCT overcomes the fundamental dose barrier in micro- CT high-resolution imaging. Further, IGMCT can be used as an important in vivo imaging modality for biology research beyond radiation oncology.

In reference to FIG. 1, an exemplary flash treatment system 100 using multipixel x-ray source is shown. In some embodiments, a small animal irradiator based on a multipixel x-ray source may be used. A plurality of cathodes 102 may be mounted on a ring structure 104, generating a plurality of focal spots on a ring shape anode 106. A multi-slot collimator 108 that is designed on the anatomy may collimate the beams to a target 110. In some embodiments, the beams may be turned on simultaneously. Additionally, or alternatively, the field strength may be modulated by a beam-on time or a beam specific compensator.

FIG. 1 illustrates an exemplary CAD design of the flash treatment system 100. In some embodiments, the flash treatment system 100 may include a rotating anode 106 having multi-pixel x-ray sources. Alternatively, the system design may include a fixed anode design. Continuing with the example shown in FIG. 1, with 100 Gy/s dose rate, a 0.2 beam-on time will deliver about 20 Gy dose. The anode may have quite a large mass to store the heat. Therefore, the major factor that limits dose rate may be the focal spot power density. Based on tungsten target x-ray production efficiency and anode angle, the requirement of beam current for each source may be calculated. Then, based on the focal spot power limitation, the focal spot size to achieve this current may be derived.

In some embodiments, the SAFI is integrated with inverse-geometry micro-CT based on circular x-ray source array. The SAFI includes a donut-shaped copper anode with 10 degree anode angle and a circular array of cathodes. In this example, the cathodes may generate 51 focal spots on the tungsten targets that are brazed on the copper anode. X-ray beams exit the inner wall of vacuum housing, then are collimated by a full-ring multi-aperture collimator (MAC) designed in treatment planning. A partial-ring MAC and a small area detector will replace the full-ring treatment MAC and rotate about the animal during imaging. All sources are activated simultaneously for FLASH-RT treatments or sequentially for IGMCT imaging. The SAFI achieves UHDR by delivering x-ray beams from 51 angles. Further, IGMCT is realized by rotating a compact small area while activating the sources in FOV sequentially.

In some embodiments, a design factor may include a distance between the center of a single source and the geometric center $d_{SC}$. In this example design, 100 mm is a quite minimal choice for the irradiator. It may be necessary for a proper-size slot collimator (40 mm) or imaging detector (50 mm), room for tube housing (30 mm) and fit in with a small animal (20 mm). The x-ray fluence may be proportional to the inverse square of the distance from the source.

Additionally, or alternatively, the x-ray fluence at the center of the irradiator may be proportional to the inverse square of the ring source radius, but the number of sources may be proportional to the radius. There may be a tradeoff between stronger x-ray intensity and a larger irradiating volume. For FLASH purpose, the more compact the sources, the higher dose rate may be achieved. From this aspect, if collimation is not considered, there is a minimum number of sources if the distance between the sources to center is minimal. For example, 30 mm tube house and 20 mm small animal radius may allow more than 60 sources with 4 mm spacing.

Figure 2:
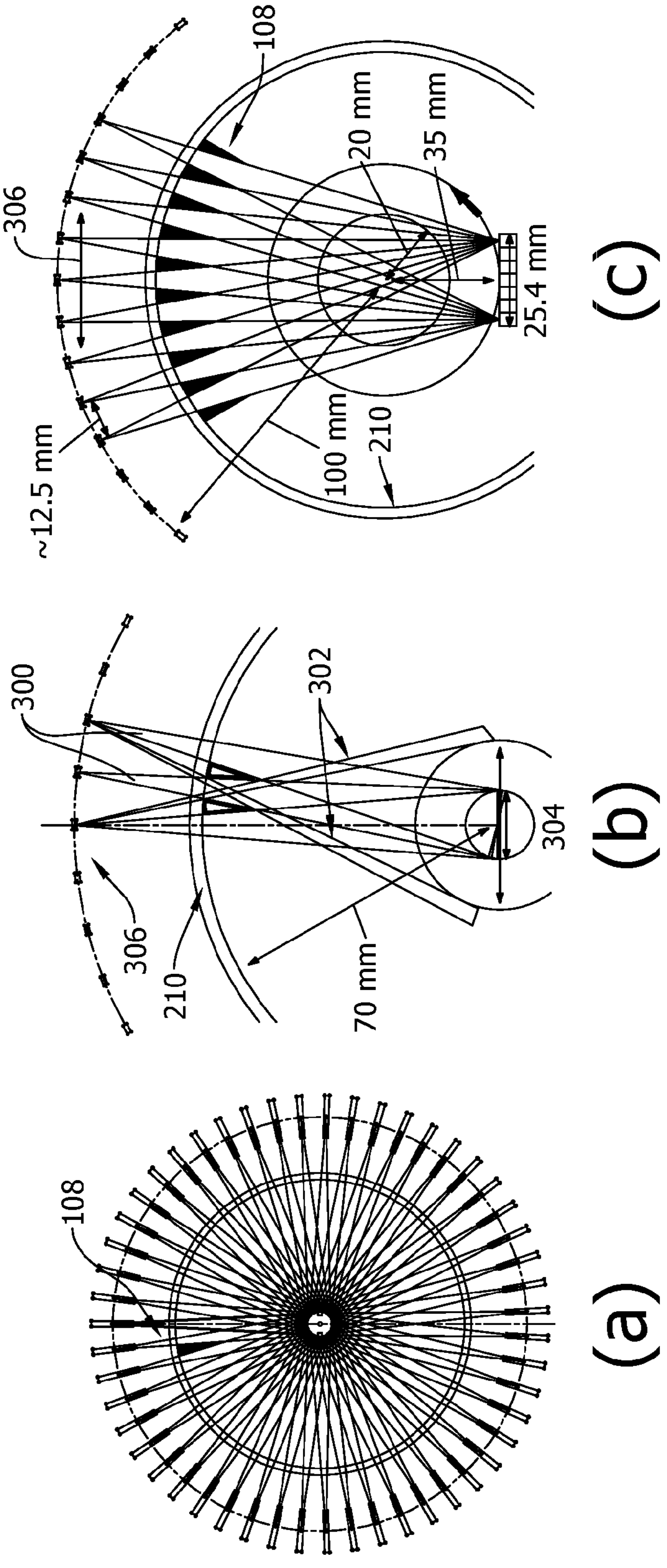
FIG. 2 depicts in (a) and (b) a MAC design for FLASH-RT and (c) inverse geometry CT where the MAC collimates the beams to the target in FLASH-RT and the detector in IGMCT and further the potential leakage caused by cross-talking between adjacent apertures limits the maximum field size.

During a FLASH-RT treatment, all beams are to be turned on simultaneously with flux intensities optimized in treatment planning. A full ring MAC will be custom designed based on the actual geometry of the target and fabricated by 3D printing techniques. The MAC will conform the beams 300 to the target while avoiding unnecessary leakage x-rays 302 produced by adjacent sources as shown in FIG. 2. The maximum field size 304 will be determined by the source to axis distance (SAD), MAC position and the number of x-ray sources 306. With 10 cm SAD and 7 cm bore diameter, the maximum field size that can be obtained at the isocenter is about 1.0-1.5 cm. Reducing the number of sources allows treatment of a larger target, but the maximum dose rate will be reduced accordingly. With 51 sources, the SAFI system can achieve a maximum dose rate at above 80 Gy/s in continuous (DC) mode and well above 100 Gy/s in pulsed mode. SAFI of course can be used for CDR-RT by reducing the tube current.

Inverse-geometry micro-CT (IGMCT): Micro-CT is broadly used in preclinical research. Small animal irradiators need onboard imaging for treatment planning and animal positioning. As shown in FIG. 2*c*, a rotatable flat small-area detector array and a MAC dedicated for imaging can be positioned in the system bore for IGMCT imaging. Similar to the full ring MAC for treatment, the arc-shaped imaging MAC conforms the x-ray beams to the detector. During imaging, the detector array and MAC will rotate synchronously in discrete steps spaced by the angular spacing between sources. At each angle, the multi-source beam controller sequentially scans the sources that can produce transmission measurement of the subject (9 sources as shown in FIG. 2*c*). Without rotating the animal or the sources, a rotation of the detector and MAC alone will generate 51 projection angles, which can only be used to reconstruct low-resolution images. To reconstruct high-resolution images for treatment planning, the source array or the animal subject also needs to rotate a few steps for acquiring more projection angles.

Additionally, or alternatively, the distributed x-ray source allows in-plane modulation of beam intensity. Traditionally, a physical bowtie filter is used to reduce the intensity of x-ray away from the central axis. But the position of the ROI varies with projection angles. IGMCT allows dynamically modulating the in-plane x-ray intensities based on the ROI positions. As shown in FIG. 2*c*, among the nine beams that produce in field-of-view, only the beams that intercept the ROI will have a higher flux. Dynamic in-plane fluence modulation can reduce unnecessary x-ray exposure to peripheral tissues and organs.

Figure 3:
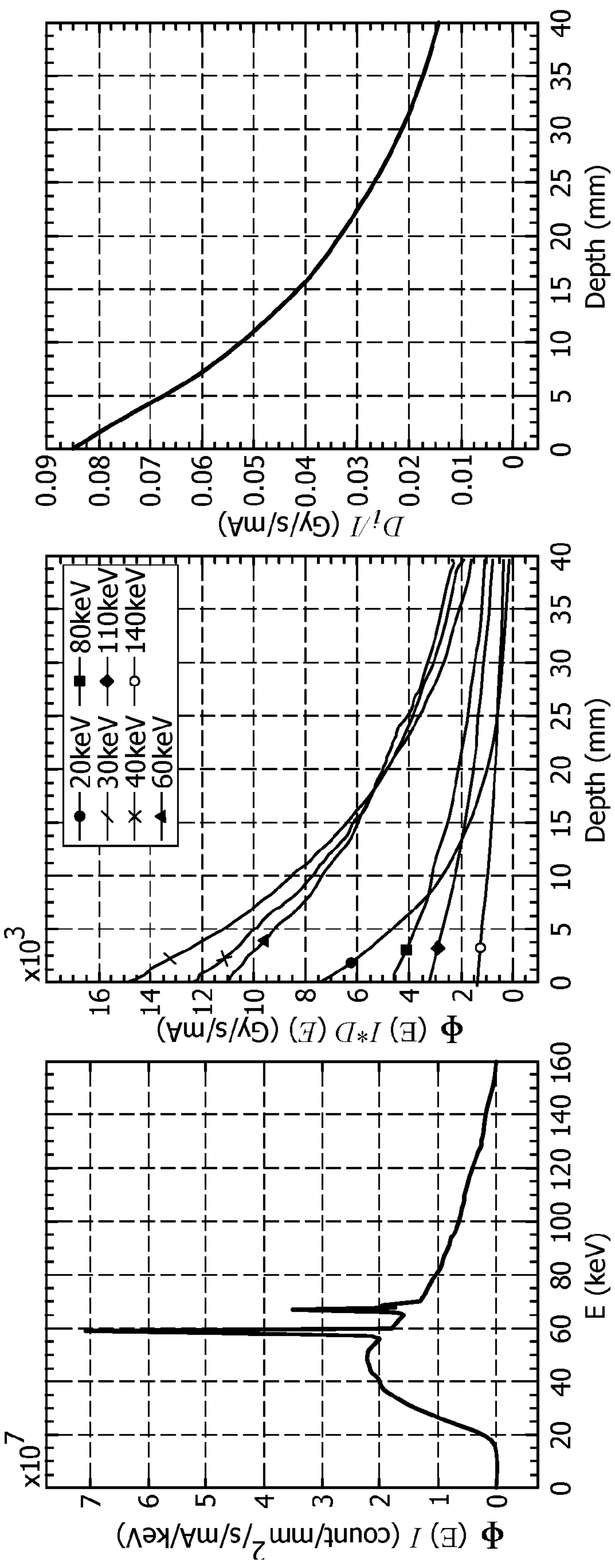
FIG. 3 illustrates exemplary results from an MC simulation including: energy spectrum of photon fluence rate (left), depth dose rate per mA current for each energy bin (middle), and total depth dose rate per mA current of entire spectrum.

In reference to FIG. 3, an exemplary requirement of cathode current for flash RT is provided. FIG. 3 illustrates exemplary results from an MC simulation including: energy spectrum of photon fluence rate (left), depth dose rate per mA current for each energy bin (middle), and total depth dose rate per mA current of entire spectrum (right).

In view of FIG. 3, the x-ray fluence rate Φ(E) produced by unit current bombarding electrons may be obtained from the MC simulation. The dose rate per mA current for the photon energy bin E vs depth from the surface of cylindrical water phantom may be plotted in FIG. 3 (middle).

Using Equation (1), the dose rate per mA current along the vertical axis of a 40-mm water phantom may be estimated.

$$\frac{\dot{D}_i}{I} \approx \sum_{E=0}^{E_{max}} \frac{\Phi(E)}{I} \cdot D(E) \tag{1}$$

The exemplary dose rate per mA current vs depth from the surface of cylindrical water phantom is plotted in FIG. 3.

The exemplary dose rate per mA is 0.0843 Gy/s/mA at the surface and 0.0335 Gy/s/mA at the center of phantom.

The required cathode current $I_{FLASH}$ may then be calculated by Equation (2).

$$I_{FLASH} = \frac{\dot{D}_{FLASH}}{N \cdot \frac{\dot{D}_i}{I}} \quad (2)$$

Required single cathode current $I_{FLASH}$ for N sources to obtain the intended dose rate $D_{FLASH}$=100 Gy/s at the center of phantom is simply 2985/N mA. In the exemplary design, FLASH dose-rate requirement $D_{FLASH}$ may be 100 Gy/s at the center of phantom, and there may be 51 sources. The required cathode current for each source $I_{FLASH}$ may be, for example, 58.5 mA.

Figure 4B:
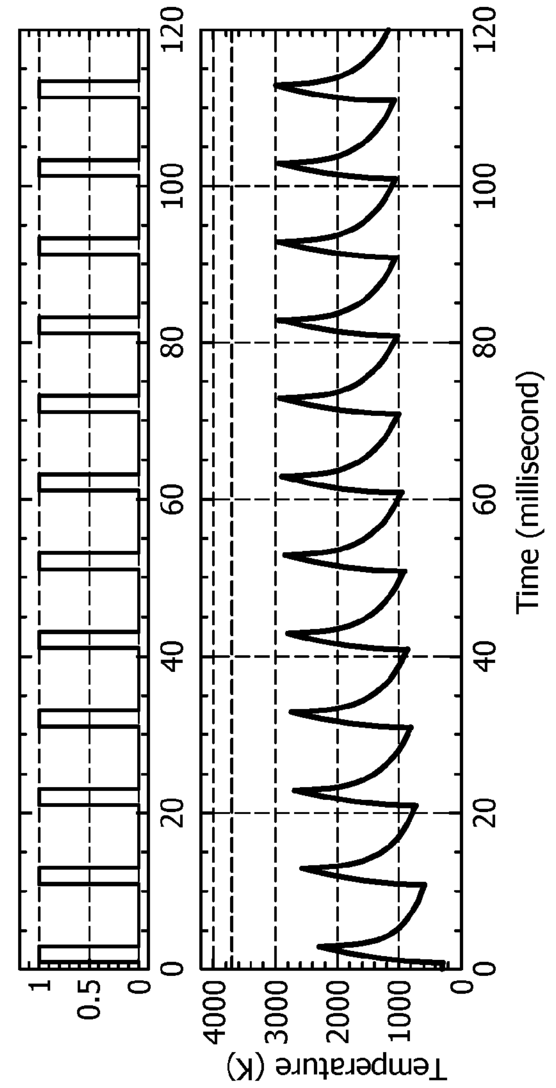
FIGS. 4A and 4B illustrate exemplary maximum input current density $I_{max}$ vs heating pulse width (4A) and temperature vs time at the center of the focal spot wherein 2-millisecond in a 10-millisecond period and 2 times more powerful pulses were applied (4B).
Figure 4A:
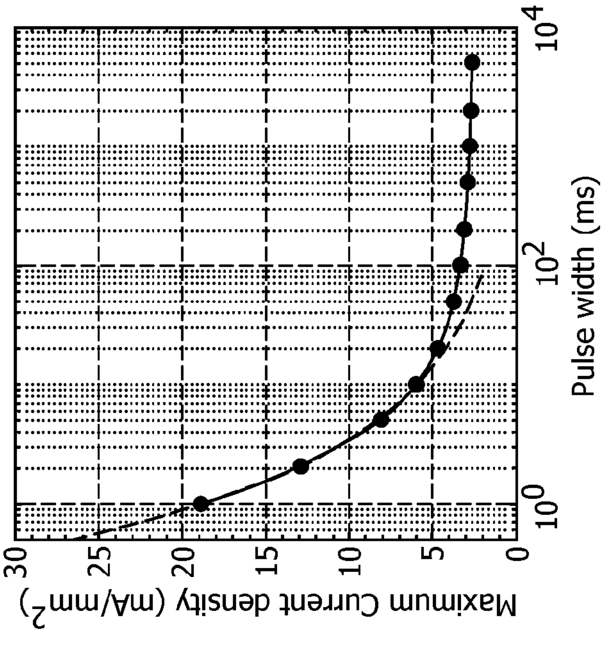

FIGS. 4A and 4B illustrate exemplary maximum input current density $I_{max}$ vs heating pulse width (4A) and temperature vs time at the center of the focal spot wherein 2-millisecond in a 10-millisecond period and 2 times more powerful pulses were applied (4B).

Figure 5C:
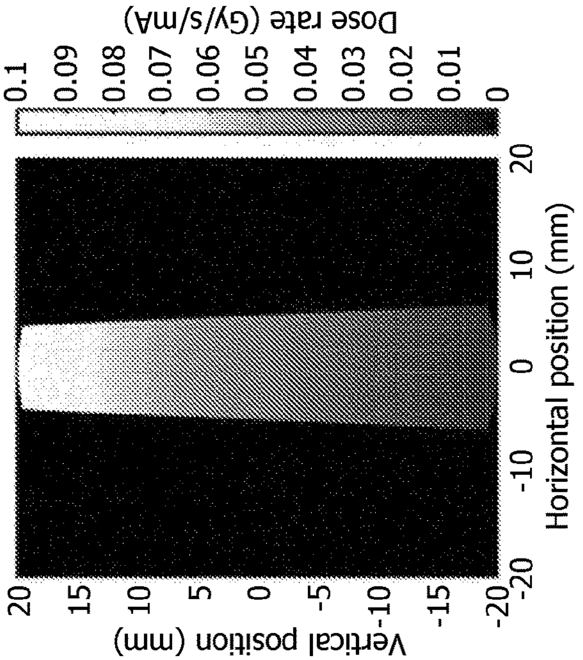
FIGS. 5A-5C illustrate an exemplary depth dose plot for a single source (5A), lateral dose distribution at 5, 20 and 35 mm depth (5B) and distribution of dose rate per cathode current from a single source (5C).
Figure 5B:
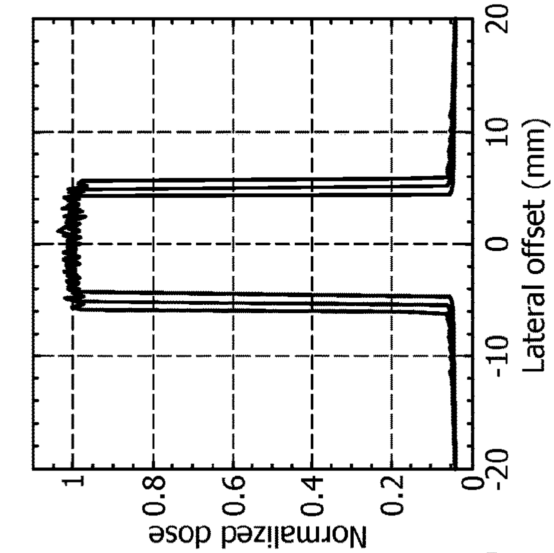
Figure 5A:
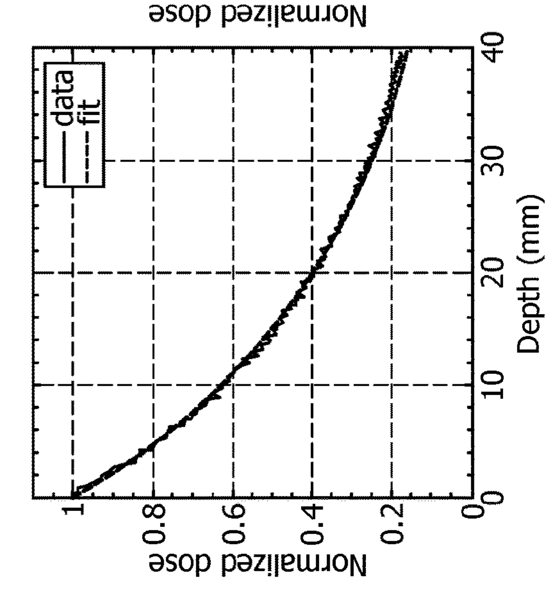

FIGS. 5A-5C provide exemplary radiation dose characteristics of a treatment beam. FIGS. 5A-5C illustrate an exemplary depth dose plot for a single source (5A), lateral dose distribution at 5, 20 and 35 mm depth (5B) and distribution of dose rate per cathode current from a single source (5C).

In some embodiments, example radiation beam properties from an ideal point source are plotted in FIGS. 5A-5C. The dose falls to 90% at 2.3 mm, 50% at 15.1 mm, and 10% at 50.0 mm. The lateral dose outside the beam region due to scattering is nearly 0%. Dose rate per cathode current for a single beam were calculated and plotted in FIGS. 5A-5C. This result may be used for optimization of a treatment plan by varying the cathode current of each source.

Figure 6B:
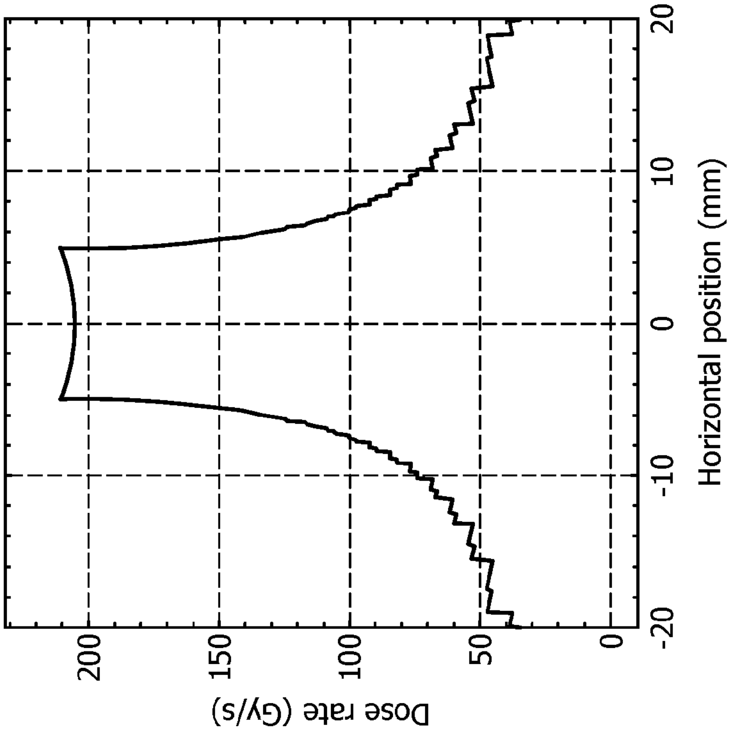
FIGS. 6A and 6B illustrate an exemplary dose distribution of an equally weighted treatment plan (6A) and the dose rate across the centerline (6B).
Figure 6A:
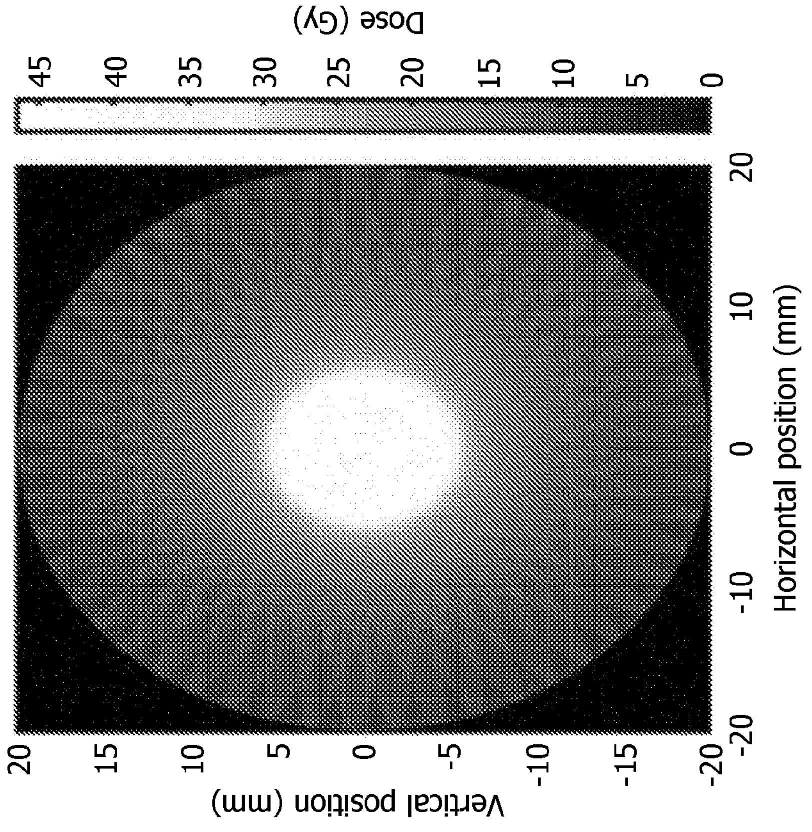

FIGS. 6A and 6B illustrate an exemplary dose distribution of an equally weighted treatment plan (6A) and the dose rate across the centerline (6B). The example shown calculated the dose distribution of a simple treatment plan. All 51 cathodes each used 120 mA cathode current (maximal for a 2×20 $mm^2$ focal spot). 40 Gy dose in a 10 mm diameter circle may be delivered with more than 200 Gy/s dose rate in a 0.2-second single pulse.

Figure 7B:
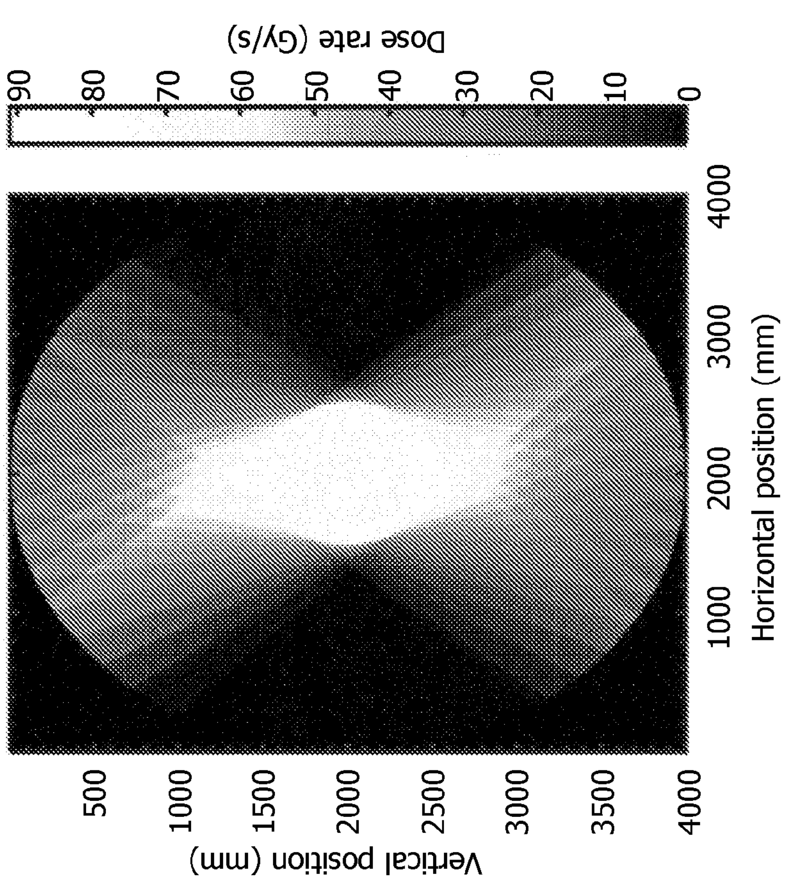
FIGS. 7A and 7B illustrate an exemplary treatment goal with target in white circle receiving 100% dose and OAR in black circles receiving as little dose as possible (7A) and dose rate distribution in a treatment plan optimized toward the treatment goal (7B).
Figure 7A:
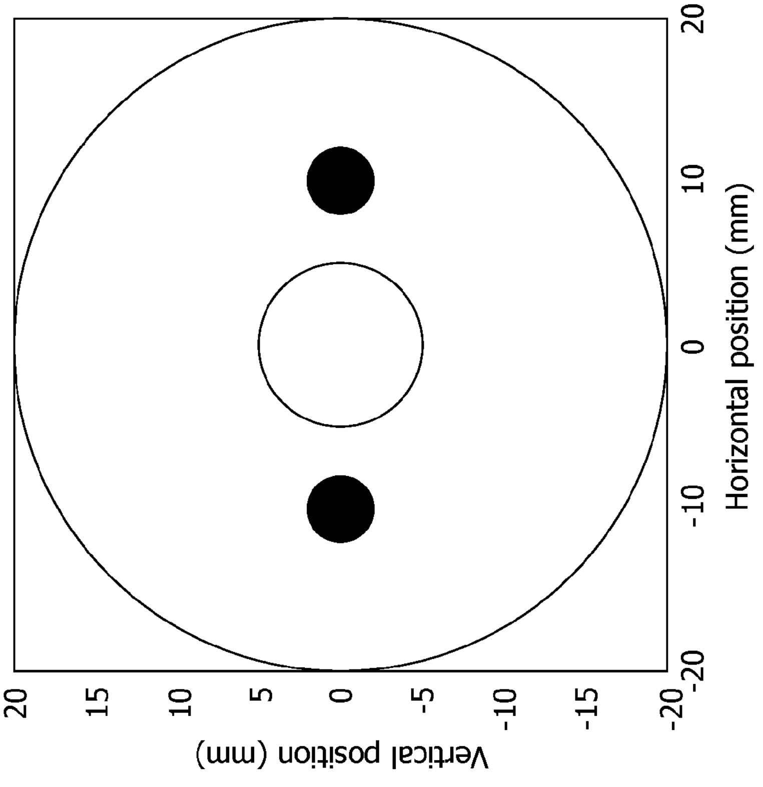

FIGS. 7A and 7B illustrate an exemplary treatment goal with target in white circle receiving 100% dose and OAR in black circles receiving as little dose as possible (7A) and dose rate distribution in a treatment plan optimized toward the treatment goal (7B). In some embodiments, a more flexible treatment plan may be operated using a kV-FLASH irradiator design. In FIGS. 7A and 7B, an example plan for a 10 mm diameter treatment target at center with two organ at risk (OAR) regions is illustrated. Dose distribution may be adjusted through beam current parameters of 51 source angles. The example directly calculates the beam current parameters by using pseudo-inverse of the dose distribution of each source angle. The uniquely determined solution of beam current parameters minimizes the square of errors to the treatment goal. In this exemplary treatment plan, most of horizontal beams are nearly off, but the dose rate of the treatment target region can still be more than 70 Gy/s, whereas the dose rate in OAR region is way below 100 mGy/s.

Figure 8:
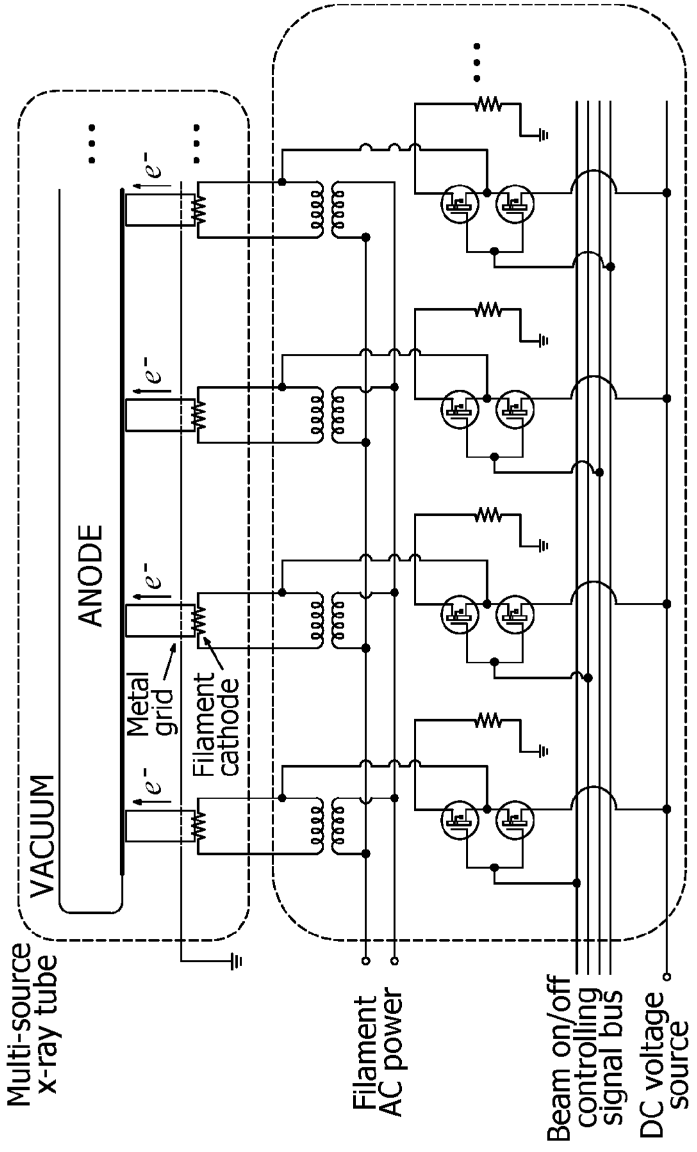
FIG. 8 illustrates an electronic control diagram in accordance with at least one embodiment.

FIG. 8 illustrates an exemplary electronic control diagram. In one embodiment, the electronic control includes a beam scanning control which may be the same as an MPTEX source. Each source can be addressed independently and turned on and off simultaneously or sequentially. In some embodiments, the electronic control of the MPTEX tube is used for TBCT. The SAFI system can use the same control for micro-CT imaging and FLASH-RT. The filament power may be provided by isolation transformers. The beam control may be developed based on a field-programmable gate array (FPGA) and fast MOSEF switches that can control beam on and off with microsecond precision. Different scanning sequences can be achieved by programming the FPGA using VHDL language. In some embodiments, the FPGA board is programmed to control the SAFI system in FLASH-RT, CDR-RT and micro-CT imaging modes of operation.

In some embodiments, IGMCT is used to realize fluence-modulated scanning with the SAFI system. The system may, for example, acquire a low-resolution image with static source positions and object and high-resolution (~100 micron) images by rotating either the source or object in 4-6 steps in addition to detector rotation. The image quality and resolution may then be evaluated.

Figure 9:
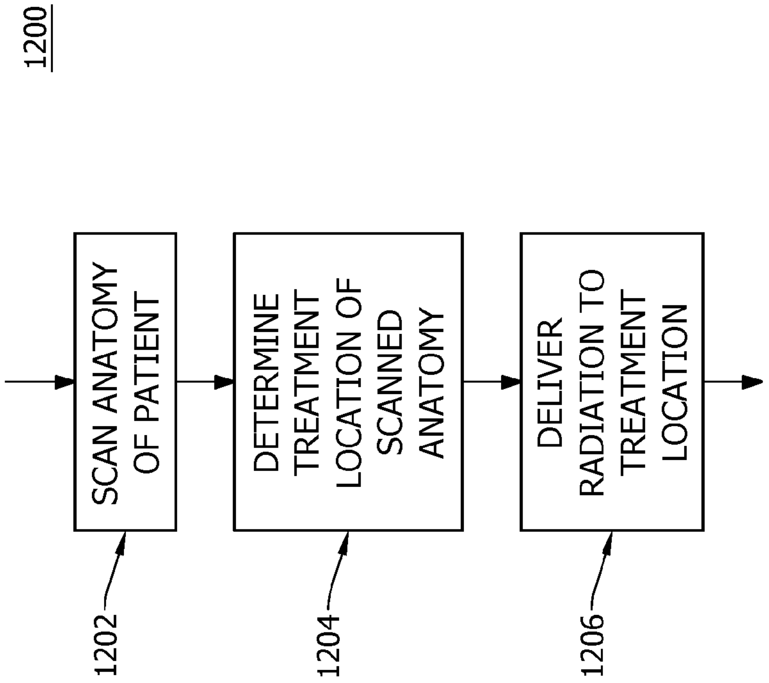
FIG. 9 illustrates an exemplary process 1200 implemented by the flash radiotherapy device.

FIG. 9 illustrates an exemplary process 1200 implemented by the flash radiotherapy device. The flash radiotherapy (RT) irradiator device having a multipixel x-ray source may be provided. The device may be used to scan 1202 an anatomy of an animal, determine 1204 a treatment location of the animal, and deliver 1206 an ultra-high dose of radiation to the treatment location. The multipixel x-ray source may include a ring of focal spots capable of irradiating x-ray beams from many beam angles. Additionally, x-ray beams may be collimated with a 3D printed collimator of the animal's anatomy.

In one embodiment, inverse-geometry micro-CT imaging may be provided. The imaging MAC can be machined using electrical discharge machining (EDM) or 3D printing. Brass may be sufficient for collimating 60 kVp x-rays. Imaging dose is the fundamental limitation of micro-CT image resolution. With each traditional in-plane fan-beam divided into multiple beam segments, the beam intensity can be modulated so that the beams intercepting the ROI will have the highest flux, thus greatly reducing the imaging dose to the volume outside the ROI. A low-resolution image may be scanned with a fixed source position first, then ROI is designed to have an image with higher quality. There are a few approaches to modulate beam intensity on the SAFI system including: 1) changing filament temperature; 2) applying gate voltage; or 3) modulating pulse width. Among them, only the pulse width can be modulated rapidly. The beam control FPGA program may be modified to optimize the x-ray flux and program the beam scan based on the optimized beam sequence. When field size is narrowly collimated, longer exposure time may be necessary as geometric efficiency is reduced. Treatment planning solutions can be used to calculate the imaging dose, which can be incorporated into the RT prescription. The image quality may be evaluated with image phantoms and dose may be measured with film.

A treatment planning solution may be needed for FLASH-RT and CDR-RT treatment of rodents with the SAFI. The SAFI is flexible in optimization parameters: 1) The beam weight can be modulated by controlling the cathode current or pulse width; 2) The aperture shapes can also be optimized to achieve optimal dose conformity; 3) In-field beam intensity can be modulated by physical compensators manufactured by 3D printing; and 4) The beam kVp can be modulated for optimal depth dose distribution. Dose calculation and optimization algorithms can be used, including the use of scripting functionality. In some embodiments, an optimization algorithm may include a simple inverse optimization algorithm based on conjugate gradient algorithm. Although the SAFI system is capable of modulating the beam fluence with a compensator, a simple beam weight optimization algorithm may be sufficient. The target and OARs may be contoured and 51 beams (can be any existing photon or proton beams) may be placed by a beam template and the blocks for the beams may be generated with user designed block margin. Then the block shape may be exported for 3D printing and dose calculation. The dose distribution of each beam may be calculated in micro-CT images, and then the beam weight may be optimized based on user defined objectives. The solution including beam weight and total dose may be evaluated.

One technical improvement of the disclosed embodiments includes a small animal FLASH-RT irradiator for emulating clinically-realistic CDR-RT and FLASH-RT treatments. Radiobiologists and radiation oncologists may use the reliable, low-cost, and compact small animal irradiator for pre-clinical study of FLASH effects. The disclosed SAFI system is based on circular distributed x-ray source technology and provides a small animal irradiator that can achieve intensity-modulated and conformal UHDR treatments to animal subjects. Further, it is a SARR irradiator based on distributed x-ray source technology.

Another technical improvement of the disclosed embodiments includes a dose efficient inverse-geometry micro-CT (IGMCT). Conventional CT and CBCT employ a physical bowtie filter to reduce imaging dose and avoid saturation of detectors. The imaging subject receives a relatively uniform radiation dose in the whole body within FOV. The modulation by bowtie filter is fixed and cannot be change based on animal's body profile and projection angle. The inverse-geometry CT allows "virtual bowtie" that can dynamically modulate the in-plane x-ray flux. Reduction of imaging dose for micro-CT is highly desired due to the ultra-fine image resolution. In CT scan, a high image resolution and contrast within an ROI. IGMCT supports dynamic x-ray fluence modulation based on the ROI positions so that only the x-ray beams intercepting the ROI have higher x-ray flux. Dynamic in-plane intensity modulation based on ROI has not been exploited before on both clinical diagnostic CT and pre-clinical micro-CT. It may greatly reduce unnecessary radiation exposure of CT imaging. SAFI provides an implementation in small animal imaging that overcomes the fundamental dose limitation on image resolution.

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, the terms "a" and "an" and "the" and similar references used in the context of describing a particular embodiment (especially in the context of certain of the following claims) are construed to cover both the singular and the plural, unless specifically noted otherwise. In some embodiments, the term "or" as used herein, including the claims, is used to mean "and/or" unless explicitly indicated to refer to alternatives only or to refer to the alternatives that are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and may also cover other unlisted steps. Similarly, any composition or device that "comprises," "has" or "includes" one or more features is not limited to possessing only those one or more features and may cover other unlisted features.

All methods described herein are performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member is referred to and claimed individually or in any combination with other members of the group or other elements found herein. One or more members of a group are included in, or deleted from, a group for reasons of convenience or patentability. When any such inclusion or deletion occurs, the specification is herein deemed to contain the group as modified thus fulfilling the written description of all Markush groups used in the appended claims.

To facilitate the understanding of the embodiments described herein, a number of terms are defined below. The terms defined herein have meanings as commonly understood by a person of ordinary skill in the areas relevant to the present disclosure. Terms such as "a," "an," and "the" are not intended to refer to only a singular entity, but rather include the general class of which a specific example may be used for illustration. The terminology herein is used to describe specific embodiments of the disclosure, but their usage does not delimit the disclosure, except as outlined in the claims.

All of the compositions and/or methods disclosed and claimed herein may be made and/or executed without undue experimentation in light of the present disclosure. While the compositions and methods of this disclosure have been described in terms of the embodiments included herein, it will be apparent to those of ordinary skill in the art that variations may be applied to the compositions and/or methods and in the steps or in the sequence of steps of the method described herein without departing from the concept, spirit, and scope of the disclosure. All such similar substitutes and modifications apparent to those skilled in the art are deemed to be within the spirit, scope, and concept of the disclosure as defined by the appended claims.

This written description uses examples to disclose the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A flash radiotherapy (RT) irradiator system, comprising:

a multipixel x-ray source array configured to generate a ring of focal spots capable of irradiating x-ray beams from a plurality of beam angles;

a flash RT device connected to the multipixel x-ray source and including a collimator, the flash RT device configured to:

scan an anatomy of an animal; and deliver, using the multipixel x-ray source and the radiation at an ultra-high dose rate to a collimator, treatment location of the scanned anatomy.

2. The flash RT irradiator system of claim 1, wherein a radius of the ring of focal points is approximately 10 cm.

3. The flash RT irradiator system of claim 1, wherein each beam of the x-ray beams is collimated with the scanned anatomy of the animal.

4. The flash RT irradiator system of claim 1, wherein the multipixel x-ray source is capable of irradiating x-ray beams from at least fifty beam angles.

5. The flash RT irradiator system of claim 1, wherein the collimator includes aperture openings for each x-ray source of the multipixel x-ray source array designed based on a treatment plan.

6. The flash RT irradiator system of claim 1, wherein each x-ray source of the multipixel x-ray source array is turned on simultaneously and the multipixel x-ray source array produces an ultra-high dose rate greater than 40 Gy/s.

7. The flash RT irradiator system of claim 1, wherein each x-ray source of the multipixel source array can be turned on sequentially and the multipixel x-ray source array produces a conventional dose rate less than 1 Gy/s.

8. The flash RT irradiator system of claim 1, wherein the multipixel x-ray source array has an x-ray source spacing of at least 4 mm.

9. A method for delivering radiation to an animal, the method comprising:

scanning, using a flash RT device including a collimator, an anatomy of an animal; and delivering, using a multipixel x-ray source array configured to generate a ring of focal spots capable of irradiating x-ray beams from a plurality of beam angles, radiation at an ultra-high dose rate to a treatment location of the scanned anatomy.

10. The method of claim 9, wherein the multipixel x-ray source array is configured to generate the ring of focal spots capable of irradiating x-ray beams from the plurality of beam angles simultaneously.

11. The method of claim 10, wherein each beam of the x-ray beams is collimated by a slot opening in the collimator that is optimized in treatment planning.

12. The method of claim 9, wherein the multipixel x-ray source array is configured to generate the ring of focal spots capable of irradiating x-ray beams from the plurality of beam angles sequentially.

13. The method of claim 9, wherein the multipixel x-ray source array is capable of irradiating x-ray beams from at least fifty beam angles.

14. The method of claim 9, wherein the collimator includes a plurality of slot openings designed in treatment planning based on anatomy of the animal.

15. An inverse-geometry micro-CT system, comprising:

a multipixel circular x-ray source array;

a rotatable detector array; and a rotatable multi-aperture collimator configured to direct x-ray beams from the multipixel x-ray source to the rotatable detector array, wherein the multi-aperture collimator is an arc shaped collimator including a plurality of slot openings configured to rotate to scan an animal.

16. The inverse-geometry micro-CT system of claim 15, where in the source array is stationary.

17. The inverse-geometry micro-CT system of claim 15, where in the rotatable detector array and multi-aperture collimator rotates together on a gantry.

18. The inverse-geometry micro-CT system of claim 15, where in the sources facing the slot openings scan sequentially at a plurality of projection angles.

19. A method of scanning small animal, the method comprising:

scanning a plurality of partial focal spots of a circular x-ray source array;

collimating, with a rotatable multi-aperture collimator, the x-ray source array to a detector;

rotating the collimator and detector to another angle;

repeating scanning the plurality of partial focal spots at the other angle; and reconstructing a plurality of 3D CT images using data measured by the detector.

* * * * *